(12) United States Patent
Yamada et al.

(10) Patent No.: US 8,646,462 B2
(45) Date of Patent: Feb. 11, 2014

(54) NON-HEATING FLAVOR INHALER

(75) Inventors: Manabu Yamada, Yokohama (JP);
Takuo Shiga, Tokyo (JP); Manabu Takeuchi, Tokyo (JP)

(73) Assignee: Japan Tobacco Inc., Tokyo (JP)

( * ) Notice: Subject to any disclaimer, the term of this patent is extended or adjusted under 35 U.S.C. 154(b) by 123 days.

(21) Appl. No.: 13/214,861

(22) Filed: Aug. 22, 2011

(65) Prior Publication Data

US 2011/0290267 A1    Dec. 1, 2011

Related U.S. Application Data

(63) Continuation of application No. PCT/JP2010/052370, filed on Feb. 17, 2010.

(30) Foreign Application Priority Data

Feb. 23, 2009   (JP) ................................. 2009-039381

(51) Int. Cl.
*A24F 13/00*   (2006.01)
*A24F 17/00*   (2006.01)

(52) U.S. Cl.
USPC ........... 131/329; 131/270; 131/273; 131/331; 128/202.22

(58) Field of Classification Search
None
See application file for complete search history.

(56) References Cited

U.S. PATENT DOCUMENTS

| | | | |
|---|---|---|---|
| 3,320,953 A | 5/1967 | Rindner | |
| 4,284,089 A * | 8/1981 | Ray | ............................... 131/270 |

(Continued)

FOREIGN PATENT DOCUMENTS

| | | |
|---|---|---|
| DE | 36 39 667 A1 | 6/1988 |
| GB | 645.517 | 11/1950 |

(Continued)

OTHER PUBLICATIONS

International Preliminary Report on Patentability (PCT/IPEA/409) dated Mar. 22, 2011.

(Continued)

*Primary Examiner* — Richard Crispino
*Assistant Examiner* — Phu Nguyen
(74) *Attorney, Agent, or Firm* — Birch, Stewart, Kolasch & Birch, LLP

(57) ABSTRACT

A non-heating flavor inhaler (1) comprises a suction holder (2) including an upstream section (10) extending from a front end thereof to a partition (4) in the suction holder (2), and a downstream section (14) extending from the front end thereof to a mouth end in the suction holder (2), the downstream section (14) having a front passage extending along the upstream section (10), an ambient air intake (12) provided in a circumferential wall of the suction holder (2) to connect the upstream section (10) to the outside, and a pouch (30) for releasing a tobacco flavor, the pouch (3) being located on the boundary between the upstream section (10) and the downstream section (14) and extending along a longitudinal axis of the suction holder (2).

16 Claims, 11 Drawing Sheets

(56) References Cited

U.S. PATENT DOCUMENTS

| | | | |
|---|---|---|---|
| 5,101,838 A | 4/1992 | Schwartz et al. | |
| 7,163,013 B2 * | 1/2007 | Harrison | 128/203.21 |
| 2005/0155601 A1 | 7/2005 | Steiner et al. | |
| 2005/0244521 A1 * | 11/2005 | Strickland et al. | 424/751 |
| 2008/0302682 A1 | 12/2008 | Engstrom et al. | |

FOREIGN PATENT DOCUMENTS

| | | |
|---|---|---|
| JP | 2-2331 A | 1/1990 |
| JP | 2-002331 A | 1/1990 |
| JP | 2-64166 A | 3/1990 |
| JP | 2-171174 A | 7/1990 |
| JP | 11-178562 A | 7/1999 |
| JP | 3137445 U | 11/2007 |
| RU | 53116 U1 | 5/2006 |
| RU | 72821 U1 | 5/2008 |

OTHER PUBLICATIONS

International Search Report, PCT/JP2010/052370, Jun. 1, 2010.
Notification about the Results of Subtantive Examination issued on Nov. 30, 2012 in Russian Patent Application No. 2011138949/14, with English translation.
Office Action issued Jan. 30, 2013, in Japanese Patent Application No. 2011.500634.
Extended European Search Report issued Jun. 6, 2012, in European Patent Application No. 10743786.5.
Canadian Office Action dated Jan. 31, 2013 for Canadian Application No. 2,752,577.

* cited by examiner

NON-HEATING FLAVOR INHALER

CROSS REFERENCE TO RELATED APPLICATIONS

This application is a Continuation of PCT International Application No. PCT/JP2010/052370 filed on Feb. 17, 2010, which claims the benefit of Patent Application No. 2009-039381 filed in Japan on Feb. 23, 2009. The entire content of all of the above applications is hereby incorporated by reference into the present application.

TECHNICAL FIELD

This invention relates to a non-heating flavor inhaler which allows the user to enjoy a flavor of tobacco or the like by inhaling air without the need for ignition.

BACKGROUND ART

Cigarettes have long been enjoyed as refreshing/relaxing articles. In recent years, however, the influence on the surroundings of sidestream smoke and odor released from a burning cigarette has been increasingly discussed.

In order to alleviate the problem, a known smokeless cigarette comprises a hollow cylindrical holder having an air intake and a mouth end, an air-permeable capsule held inside the holder, and tobacco materials impregnated with flavoring constituents of tobacco, packed in the capsule (patent document 1). Such smokeless cigarette allows the user to enjoy a tobacco flavor by inhaling air having passed through the capsule.

PRIOR-ART DOCUMENT

Patent document 1: Japanese Patent Application Laid-open No. Hei 2-2331 Publication

SUMMARY OF THE INVENTION

Problem to be Solved by the Invention

In the smokeless cigarette disclosed in patent document 1, the capsule is in the form of a cylinder extending along the axis of the holder and air-permeable only at the ends facing the air intake and the mouth end, respectively. Thus, the user's sucking on the mouth end causes air to flow through the capsule, in the direction of axis of the holder, where the cross-sectional area of flow of the air passing through the capsule is restricted by the cross-sectional area of the capsule, and thus, of the holder.

This results in a small area of contact between air passing through the capsule and tobacco materials, and thus, does not allow the user to enjoy a satisfactory flavor when inhaling air.

In order to overcome such problem, packing tobacco materials in the capsule at an increased density, or use of a capsule with a greater axial length is conceivable. These measures however cause to the user a feeling of strangeness as compared with cigarettes.

An object of the present invention is to provide a non-heating flavor inhaler which provides a great area of contact between air and flavor-releasing materials, such as tobacco materials, and allows the user to easily inhale air with flavoring substances released from a flavor releasing source.

Means for Solving the Problem

In order to achieve the above object, a non-heating flavor inhaler comprises a hollow suction holder having a longitudinal axis, a front end and a rear end serving as a mouth end, and defining an air passage therein for allowing ambient air taken in at a front end side to flow to the mouth end; a flavor releasing source arranged in the suction holder, the flavor releasing source being air-permeable and capable of releasing flavoring substances in the air passage without being ignited; and a support device for supporting the flavor releasing source in the suction holder such that the flavor releasing source divides the air passage into a front end-side upstream section and a mouth end-side downstream section, the support device allowing the flavor releasing source to expose to at least one of the upstream section and downstream section, wherein an exposing area of the flavor releasing source is greater than a cross-section of the suction holder delimited by a inner circumference thereof.

The flavor releasing source may extend along the longitudinal axis of the suction holder from the front end thereof to divide the air passage with respect to the radial direction of the suction holder.

The upstream section may include an ambient air intake provided in at least one of a circumferential wall and a front end wall of the suction holder to allow ambient air to flow in toward the flavor releasing source.

In such flavor inhaler, the user's sucking on the mouth end of the suction holder causes ambient air to flow in toward the flavor releasing source via the ambient air intake in the suction holder, then through the flavor releasing source, with respect to the radial direction of the suction holder, to the downstream section. The arrangement of the flavor releasing source allowing a surface greater in area than the cross-section of the suction holder delimited by the inner circumference thereof to be exposed to air results in the air's sufficiently contacting the flavor releasing source, and thus, sufficiently containing flavoring substances released from the flavor releasing source. The air then flows in the downstream section to the mouth end, and then into the user's mouth.

The user can thus enjoy the flavor satisfactorily, by inhaling the air sufficiently containing the flavoring substances.

The suction holder may include a pair of half pipes separable from each other along a plane containing the longitudinal axis. This renders the suction holder openable and closable to allow easy replacement of the flavor releasing source.

The flavor releasing source may be integrally joined to one of the half pipes, and the suction holder may further include a hinge connecting the half pipes in a manner allowing the half pipes to be opened and closed.

The suction holder may further include a partition determining a position of a mouth end-side end of the flavor releasing source, so that the downstream section includes a front passage extending from the front end of the suction holder up to the partition, along the upstream section, and a rear passage extending from the front passage to the mouth end.

The upstream section may include a space provided between the inner surface of the suction holder and the flavor releasing source. In this case, the user's sucking on the mouth end of the suction holder causes ambient air to first flow into the space, which constitutes the upstream section, via the ambient air intake in the suction holder, then from all parts of the space into the flavor releasing source, then through the flavor releasing source in the radial direction of the suction holder, to the downstream section. The air therefore passes through the flavor releasing source, uniformly in all parts of its length along the longitudinal axis of the suction holder. This allows the air to sufficiently contact the flavor releasing source, and thus, sufficiently contain flavoring substances released from the flavor releasing source.

The suction holder may include a holder body providing a part of the suction holder from the front end up to the front passage of the downstream section, and a mouthpiece providing the rear passage of the downstream section, the mouthpiece being separably connected to the holder body.

The holder body may have a pair of half pipes separable from each other along a plane containing the longitudinal axis, and the flavor releasing source may be integrally joined to one of the half pipes.

Desirably, the holder body further has a hinge connecting the half pipes in a manner allowing the half pipes to be opened and closed.

The flavor releasing source may include a pouch having particles obtained by shredding or shattering tobacco leaves, and an air-permeable wrapper covering the particles therein.

The flavor releasing source may further include a holder frame for holding the pouch. The holder frame can prevent the pouch from moving in the suction holder.

Effect of the Invention

The present invention can provide a great area of contact between the flavor releasing source and air, and allows the user to easily inhale air with flavoring substances released from the flavor releasing source.

BEST MODE OF CARRYING OUT THE INVENTION

Figure 1:
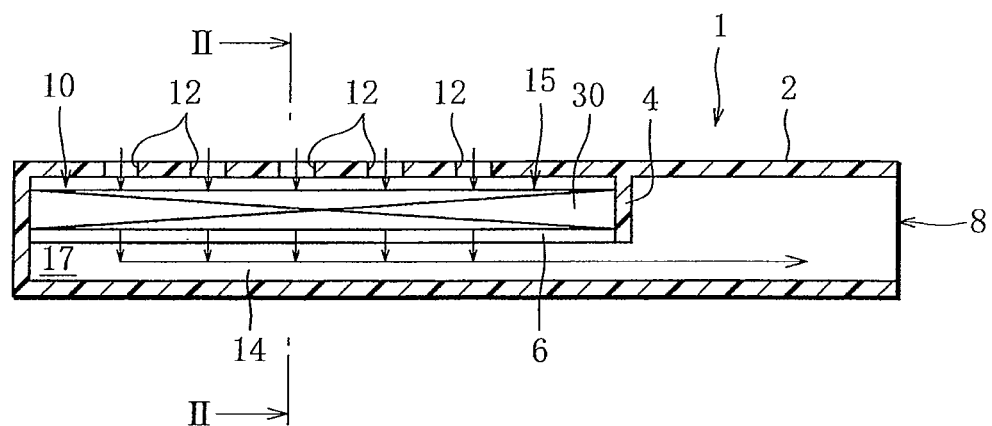
FIG. 1 is a cross-sectional view of an embodiment of a flavor inhaler according to the present invention, categorized as group A.
Figure 2:
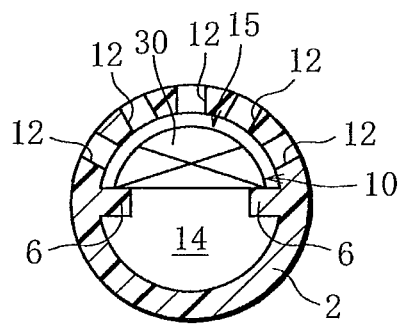
FIG. 2 is a cross-sectional view along line II-II of FIG. 1.

As seen in FIGS. 1 and 2, a non-heating flavor inhaler 1 according to embodiment A(1) includes a suction holder 2 of synthetic resin. The suction holder 2 is in the form of a hollow cylinder open at a rear, or proximal end and closed at a front, or distal end, thus having a front wall. The rear end of the suction holder 2 serves as a mouth end 8.

The suction holder 2 has a semicircular partition 4 inside. The partition 4 is located on the mouth end 8 side of the suction holder 2. The partition 4 protrudes from the inner surface of the suction holder 2 to close approximately half the cross-section of the suction holder 2. The suction holder 2 also has a pair of ribs 6 on the inner surface. The ribs 6 are arranged to face each other with the longitudinal axis of the suction holder 2 interposed between, and extend from the inside edge of the partition 4 up to the front wall of the suction holder 2, parallel to the longitudinal axis of the suction holder 2.

As a flavor releasing source, a bag called a pouch 30, filled with tobacco, is arranged on the ribs 6. Specifically, the pouch 30 extends from the front wall of the suction holder 2 up to the partition 4, along the longitudinal axis of the suction holder 2, and has a width approximately equal to the inside diameter of the suction holder 2.

By the pouch 30 and the partition 4, the inside of the suction holder 2 is divided into an upstream section 10 and a downstream section 14. The upstream section 10 is a section delimited by the front wall of the suction holder 2, the partition 4, the pouch 30 and a part of the inner surface of the suction holder 2 extending between the front wall and the partition 4, while the downstream section 14 extends from the front wall of the suction holder 2 up to the mouth end 8. Specifically, the downstream section 14 comprises a front passage semicircular in cross-section and extending along the upstream section 10, and a rear passage circular in cross-section and extending from the front passage up to the mouth end 8. The area of the surface of the pouch 30 exposed on the upstream section 10 side is thus sufficiently greater than the cross-sectional area of the suction holder 2 determined by the inside diameter of the suction holder 2.

The pouch 30 is fixed on the ribs 6 in a pair, with its side edges seated on the respective ribs 6, and thus, immovable inside the upstream section 10. It is to be noted that, with the pouch 30 set to delimit the upstream section 10, a space 15 of a predetermined size extends from the front wall of the suction holder 2 up to the partition 4, between the circumferential wall of the suction holder 2 and the pouch 30, as seen in FIGS. 1 and 2.

Figure 3:
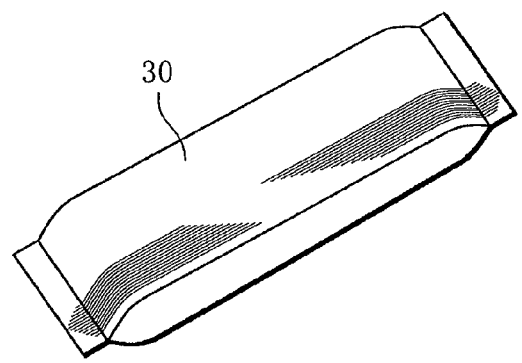
FIG. 3 is a perspective view of a pouch constituting a flavor releasing source.

As shown in FIG. 3, the pouch 30 has particles obtained by shredding or shattering tobacco leaves, and a flexible and air-permeable wrapper made of nonwoven fabric or the like, and covering the particles.

The suction holder 2 has ambient air intakes 12 in the circumferential wall. The ambient air intakes 12 are distributed in a region of the upstream section 10 to connect the upstream section 10 to outside the suction holder 2. The suction holder 2 thus provides an air passage 17 connecting the ambient air intakes 12 to the mouth end 8, via the upstream section 10 and the downstream section 8.

In the above-described flavor inhaler 1, the user's sucking on the mouth end 8 of the suction holder 2 causes ambient air to flow first into the upstream section 10, or space 15, via the ambient air intakes 12 in the suction holder 2, then from all parts of the space 15 into the pouch 30, and then through the pouch 30, in the radial direction of the suction holder 2, to the downstream section 14, as indicated by arrows in FIG. 1. Air thus passes through the pouch 30, uniformly in all parts of its length along the longitudinal axis of the suction holder 2. This allows the air to sufficiently contact the particles in the pouch 30, and thus, sufficiently contain flavoring constituents of tobacco released from the flavor releasing source. The air then flows in the downstream section 14 to the mouth end 8, and then into the user's mouth.

The user can thus enjoy the tobacco flavor satisfactorily, by inhaling the air sufficiently containing the flavoring constituents of tobacco.

Next, different embodiments of the flavor inhaler will be described, where members and parts identical in function to those in the above-described embodiment will be assigned the same reference characters to omit the explanation thereof.

Figure 4:
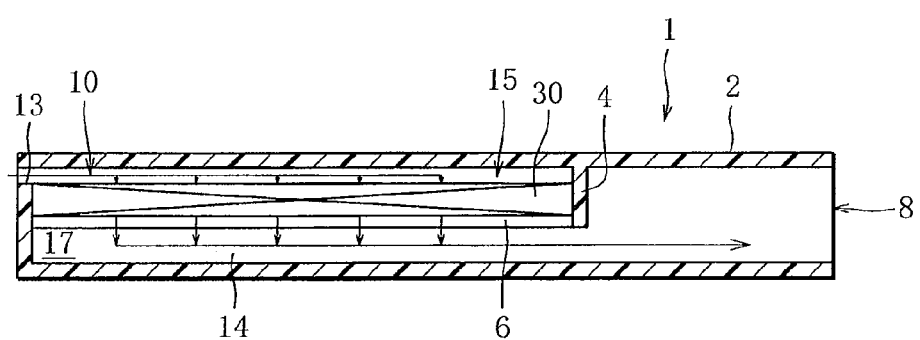
FIG. 4 is a cross-sectional view of another embodiment categorized as group A.

A flavor inhaler 1 according to embodiment A(2) shown in FIG. 4 differs from the flavor inhaler 1 according to embodiment A(1) only in that it has at least one ambient air intake 13 in place of the ambient air intakes 12. Specifically, the flavor inhaler 1 according to embodiment A(2) has an ambient air intake 13 in the front wall of the suction holder 2, which connects the space 15 constituting the upstream section 10 to outside the suction holder 2.

In the flavor inhaler 1 according to embodiment A(2), the user's sucking action causes ambient air to flow first into the space 15 constituting the upstream section 10, via the ambient air intake 13, then from the space 15 into the pouch 30, and through the pouch 30, uniformly in all parts of its length along the longitudinal axis of the suction holder 2, as in embodiment A(1). This allows the air to sufficiently contain flavoring constituents of tobacco released from the particles in the pouch 30.

Figure 5:
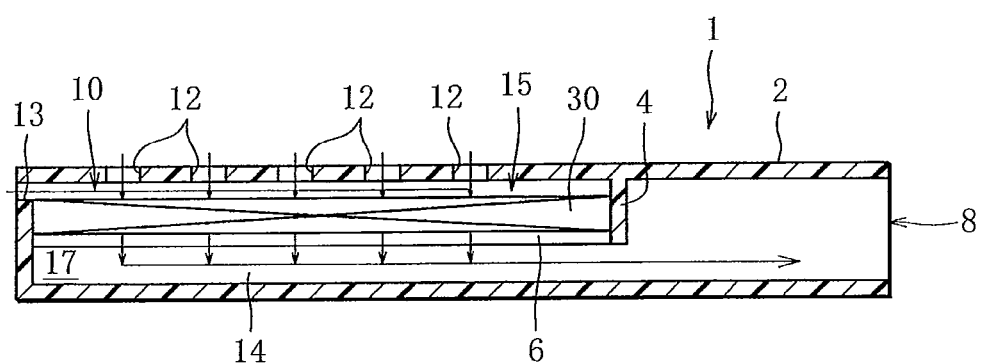
FIG. 5 is a cross-sectional view of another embodiment categorized as group A.

A flavor inhaler 1 according to embodiment A(3) shown in FIG. 5 has both the ambient air intakes 12 as seen in embodiment A(1) and the ambient air intake 13 as seen in embodiment A(2). In this flavor inhaler 1, the user's sucking action causes ambient air to flow into the space 15 constituting the upstream section 10, both in the direction of longitudinal axis of the suction holder 2 and in the radial direction thereof. The flavor inhaler 1 according to embodiment A(3) has the same advantage as the preceding embodiments have.

Figure 6:
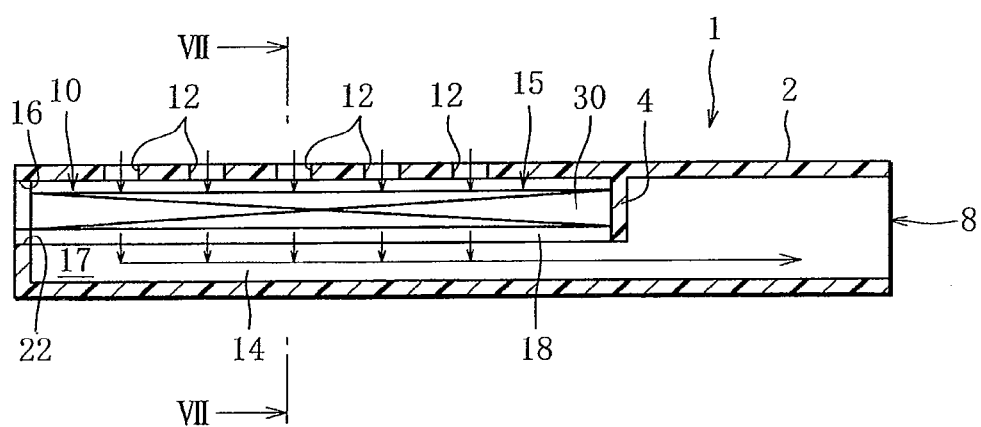
FIG. 6 is a cross-sectional view of an embodiment of a flavor inhaler categorized as group B.

A flavor inhaler 1 according to embodiment B shown in FIG. 6 differs from embodiment A(1) only in a pouch 30 support structure in the suction holder 2.

Figure 7:
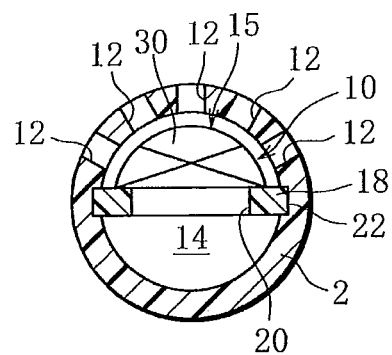
FIG. 7 is a cross-sectional view along line VII-VII of FIG. 6.

Specifically, embodiment B has a semicircular removal opening 16 in the front wall of the suction holder 2. The removal opening 16 allows access to the upstream section 10 from outside the suction holder 2. As seen in FIG. 7, the suction holder 2 has a pair of grooves 22 in the inner surface, in place of a pair of ribs 6. The grooves 22 face each other with the longitudinal axis of the suction holder 2 interposed between, and extend from the removal opening 16 of the suction holder 2 up to the partition 4, parallel to each other.

Figure 8:
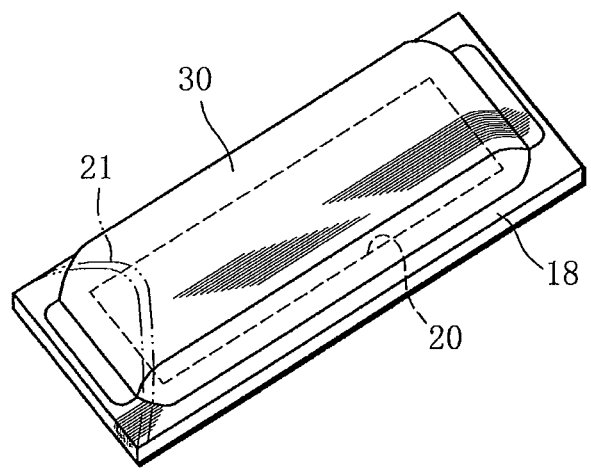
FIG. 8 is a perspective view of a pouch with a support plate shown in FIG. 6.

Further, as shown in FIG. 8, the pouch 30 is fixed on a rectangular holder frame 18. The holder frame 18 has a thickness somewhat less than the width of the groove 22 and a width slightly less than the bottom-to-bottom distance between the two grooves 22. The holder frame 18 has an opening 20 allowing the pouch 30 to be exposed on the downstream section 14 side. The opening 20 is smaller in width and length than the pouch 30.

The pouch 30 attached to the holder frame 18 can be removably set to delimit the upstream section 10, through the removable opening 16. Specifically, the removable opening 16 allows the user to engage the side edges of the holder frame 18 with the respective grooves 22, and then push the holder frame 18 with the pouch 30 fixed on, into the suction holder 2 along the grooves 22, thereby setting the pouch 30 with the holder frame 18, to delimit the upstream section 10.

In the flavor inhaler 1 according to embodiment B, the user's sucking action causes ambient air to flow first into the space 15 constituting the upstream section 10, via the ambient air intakes 12 and the removal opening 16, and then through the pouch 30 uniformly in all parts of the pouch 30. Thus, also the flavor inhaler 1 according to embodiment B can provide a tobacco flavor to the user, satisfactorily. Further, the flavor inhaler 1 according to embodiment B allows the removal of the pouch 30 from inside the suction holder 2. Thus, when the pouch 30 releases a reduced amount of flavoring constituents of tobacco, the user can replace only the pouch 30 or the pouch 30 with the holder frame 18 with a new one.

Figure 9:
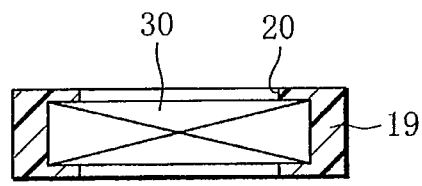
FIG. 9 is a cross-sectional view of another example of a pouch with a support plate.

The holder frame 18 may be replaced with a pocket-type holder frame 19 shown in FIG. 9. This holder frame 19 is designed to hold the pouch 30 inside, and has an opening 20 allowing the pouch 30 to be exposed on both the space 15 side and the downstream section 14 side.

Figure 10:
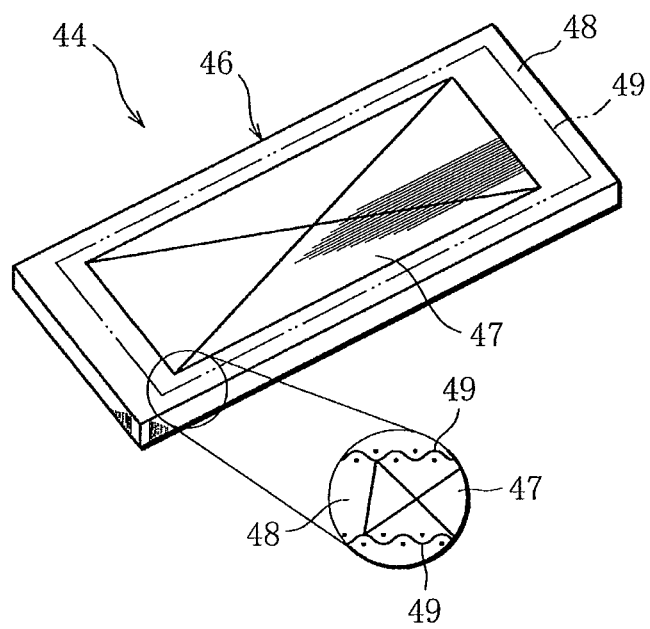
FIG. 10 is perspective view of another example of a pouch with a support plate.

The pouch 30 with the holder frame (18 or 19) may be replaced with a single cartridge 44 as shown in FIG. 10. The cartridge 44 comprises an air-permeable case 46 and particles 47 filling the case 46. Specifically, the case 46 is composed of a holder frame 48 similar in shape to the holder frame 18 and air-permeable sheets 49 arranged to cover an opening of the holder frame 48 on either side of the holder frame 48. The air-permeable sheets 49 may be, for example nonwoven-fabric or mesh sheets.

The holder frames 18, 19, 48 may be provided with a semicircular lid 21 designed to cover the removal opening 16 when the holder frame 18, 19, 48 is set to delimit the upstream section 10. The lid 21 is depicted by two-dot chain lines in FIG. 8. If the lid 21 has a tab (not shown) on the outside, it facilitates the removal of the holder frame 18, 19 or 48 from the suction holder 2.

Figure 11:
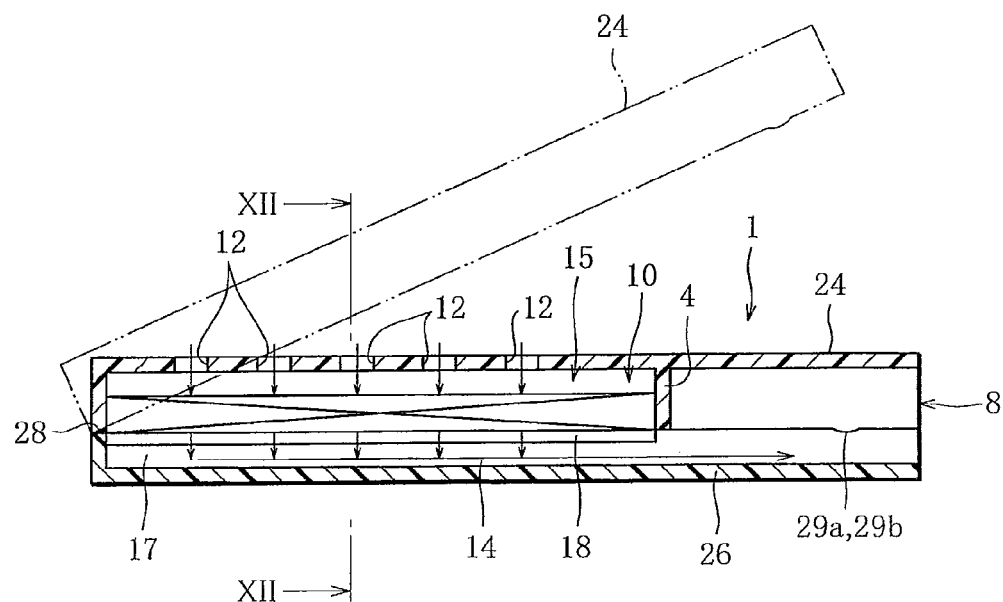
FIG. 11 is a cross-sectional view of an embodiment of a flavor inhaler categorized as group C.

A flavor inhaler 1 according to embodiment C(1) shown in FIG. 11 has an openable and closable suction holder 2. Specifically, the suction holder 2 is composed of half pipes 24, 26. The half pipe 24 provides the partition 4, the upstream section 10, a part of the downstream section 14 and the ambient air intakes 12, while the half pipe 26 provides the rest of the downstream section 14.

Figure 12:
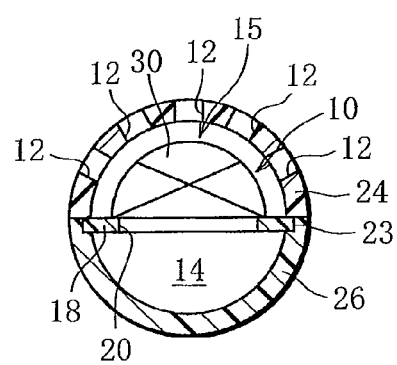
FIG. 12 is a cross-sectional view along line XII-XII of FIG. 11.

The half pipe 26 has two grooves 23, equivalent to the aforementioned groves 22, in the inner surface. Specifically, the grooves 23 extend at the opening-delimiting two side edges of the half pipe 26, parallel to the longitudinal axis of the suction holder 2, respectively. As seen in FIG. 12, each groove 23 is open at the side facing the longitudinal axis and the side facing the side edge of the half pipe 24.

The half pipes 24, 26 are connected by a self-hinge 28, at the front end of the suction holder 2. The half pipe 26 is opened or closed by turning the half pipe 24 on the self-hinge 28, relative to the half pipe 26. In FIG. 11, the half pipe 24 in an open position is depicted by two-dot chain lines.

One of the half pipes 24, 26 has a recess 29a in each side edge, while the other has a corresponding projection 29b on each side edge. Thus, with the half pipes 24, 26 butted against each other to close the suction holder 2, each projection 29b engages with the corresponding recess 29a. Such engagement between the recess 29a and the projection 20b prevents the suction holder 2 from opening accidentally, and stably keeps the suction holder 2 closed.

As seen in FIG. 12, in the closed suction holder 2, the holder frame 18 with the pouch 30 attached is set to delimit the upstream section 10, with the side edges fitted in the respective grooves 23, and thus, sandwiched between the side edges of the half pipes 24, 26. The pouch 30 is thus held immovable inside the upstream section 10, so that the space 15 constituting the upstream section 10 is reliably provided between the inner surface of the half pipe 24 and the pouch 30. Consequently, also in the flavor inhaler 1 according to embodiment C(1), the user's sucking action causes air to flow through the pouch 30 uniformly in all parts thereof. The user can therefore satisfactorily enjoy the tobacco flavor released from the particles in the pouch 30.

Further, the suction holder 2 designed to be openable and closable allows easy replacement of the pouch 30.

Figure 13:
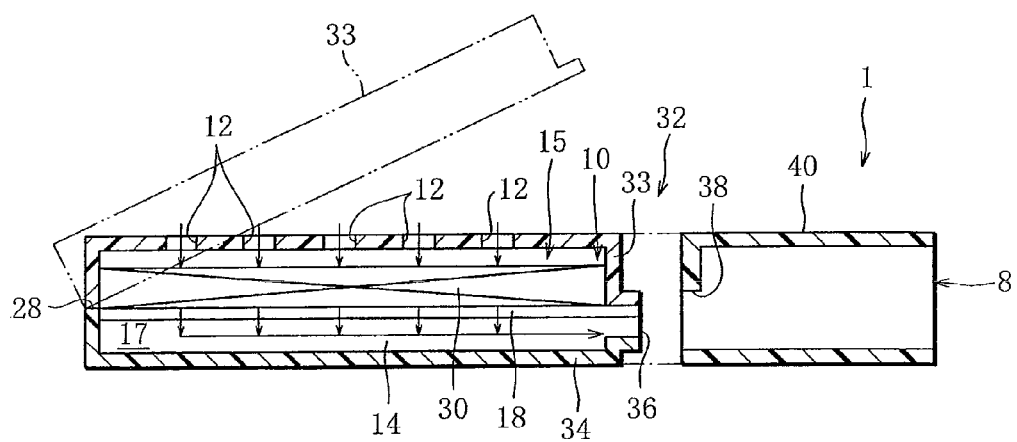
FIG. 13 is a cross-sectional view of another embodiment categorized as group C.

A flavor inhaler 1 according to embodiment C(2) shown in FIG. 13 has a suction holder 2 comprising a holder body 32 and an integrally-molded mouthpiece 40 providing a mouth end 8. The holder body 32 and the mouthpiece 40 are separably connected together.

Specifically, the holder body 32 comprises half pipes 33, 34 similar to the half pipes 24, 26 shown in FIGS. 11 and 12. The half pipes 33, 34 are connected by a self-hinge 28, at the front end of the holder body 32.

The half pipes 33, 34 each have a projection on the rear end face. With the half pipes 33, 34 butted against each other to close the holder body 32, the projections form a tubular joint 36. The tubular joint 36 is connected to the front passage of the downstream section 14. Incidentally, the rear wall of the half pipe 33 serves as the aforementioned partition 4.

The mouthpiece 40 has a hole 38 at the front end. The tubular joint 36 is adapted to be able to be inserted in or pulled out of the hole 38. By inserting the tubular joint 36 in the hole 38, the mouthpiece 40 and the holder body 32 are separably connected together.

The flavor inhaler 1 according to embodiment C(2) allows the user to satisfactorily enjoy the tobacco flavor, as the flavor inhalers 1 according to the preceding embodiments do. In embodiment C(2) in which the tubular joint 36 of the holder body 32 is inserted in the hole 38 in the mouthpiece 40, the half pipes 33, 34 do not need to have a recess 29a or a projection 29b.

The flavor inhalers 1 according to embodiments C(1), (2) may be arranged such that the suction holder 2 or the holder body 32 has a self-hinge 28 extending along the longitudinal axis, on the side wall.

Figure 14:
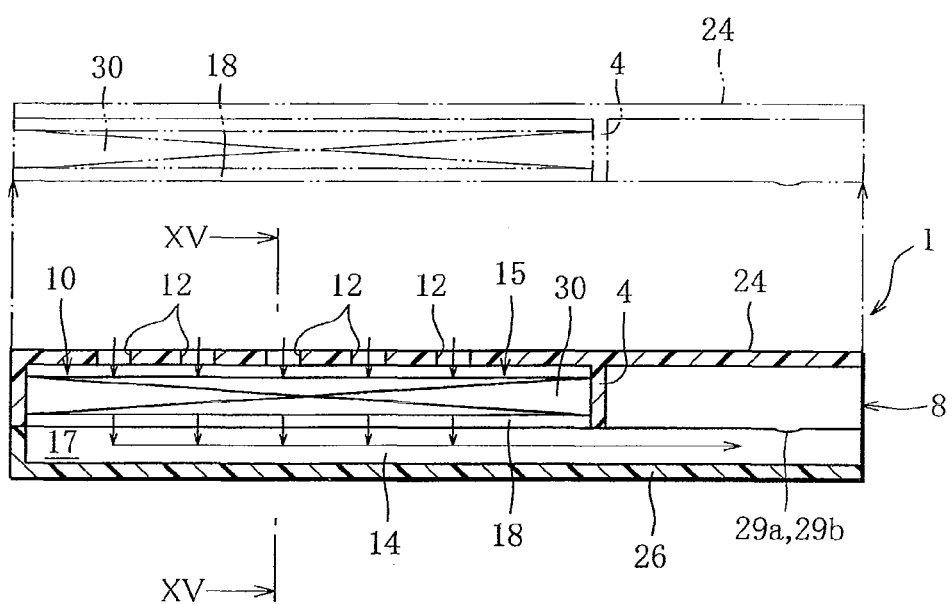
FIG. 14 is a cross-sectional view of another embodiment categorized as group C.
Figure 15:
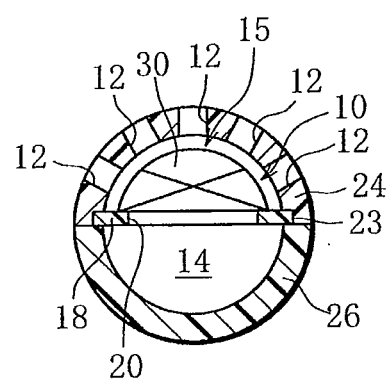
FIG. 15 is a cross-sectional view along line XV-XV of FIG. 14.

A flavor inhaler 1 according to embodiment C(3) shown in FIGS. 14 and 15 differs from embodiment C(1) in that the half pipe 24 has grooves 23. Specifically, each groove 23 is open at the side facing the longitudinal axis and the side facing the side edge of the half pipe 26. The holder frame 18 is fitted in the grooves 23, thereby separably joined to the half pipe 24. The half pipes 24, 26 are connected together only by means of a recess 29a and a projection 29b.

In the flavor inhaler 1 according to embodiment C(3), the holder frame 18 is integrally joined to the half pipe 24. Thus, when the half pipe 24 is lifted to open the suction holder 2, the pouch 30 fixed on the holder frame 18 is lifted with the half pipe 24. In this embodiment, the pouch 30 is replaced by replacing the half pipe 24 with a new one 24.

Also the flavor inhaler 1 according to embodiment C(2) may be arranged such that the half pipe 33 has grooves 23.

Figure 16:
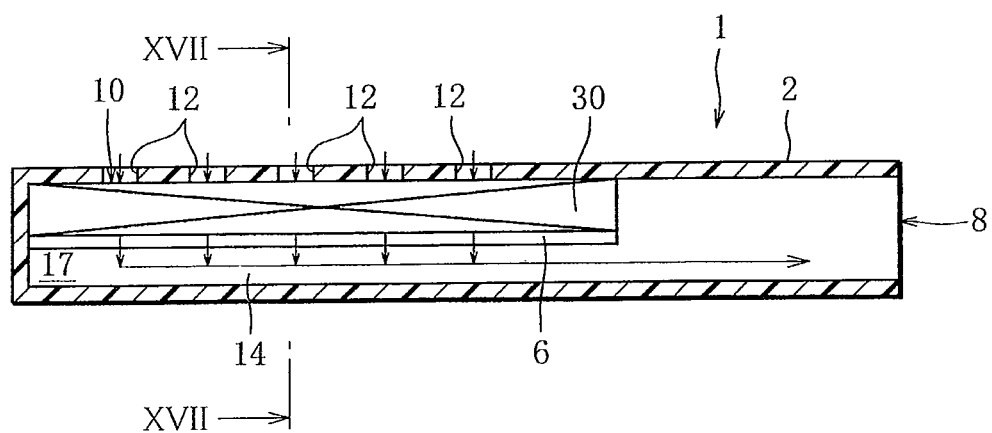
FIG. 16 is a cross-sectional view of an embodiment of a flavor inhaler categorized as group D.
Figure 17:
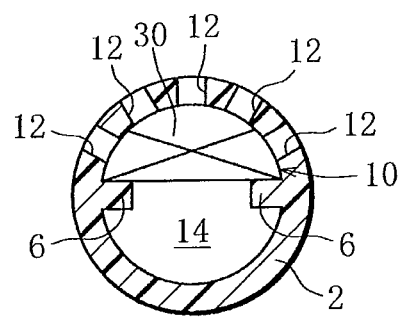
FIG. 17 is a cross-sectional view along line XVII-XVII of FIG. 16.

A flavor inhaler 1 according to embodiment D shown in FIGS. 16 and 17 differs from the flavor inhaler 1 according to embodiment A(1) in that it has neither a partition 4 nor a space 15. The pouch 30 is arranged on the front end side of the suction holder 2 in contact with the inner surface of the suction holder 2. Specifically, the pouch 30 is placed on ribs 6 in a pair and bonded to the inner surface of the suction holder 2, on the upper side, for example by an adhesive. The ribs 6 extend up to the mouth end 8 side end of the pouch 30. Ambient air intakes 12, which constitute an upstream section 10, are provided in the circumferential wall of the suction holder 2, in a region where the pouch 30 contacts the inner surface of the suction holder 2.

Also in the flavor inhaler 1 according to embodiment D, the user's sucking on the mouth end 8 causes air to flow into the suction holder, toward the pouch 30, via the ambient air intakes 12, and through the pouch 30 in the radial direction of the suction holder 2, to the downstream section 14. In this embodiment, the pouch 30 is not densely packed with particles. The air therefore passes through the pouch 30, sufficiently contacting particles in the pouch 30, in a manner such that the area of contact between air and particles increases toward the downstream section 14 side. This allows the air to sufficiently contain flavoring constituents of tobacco released from the pouch 30.

The flavor releasing source 30 may set in the suction holder 2 only by means of an adhesive, without being supported by the ribs 6 in a pair. Also the flavor inhalers 1 according to the embodiments categorized as group C may be arranged such that the flavor releasing source 30 is bonded to the inner surface of the half pipe 24 or 33.

Figure 18:
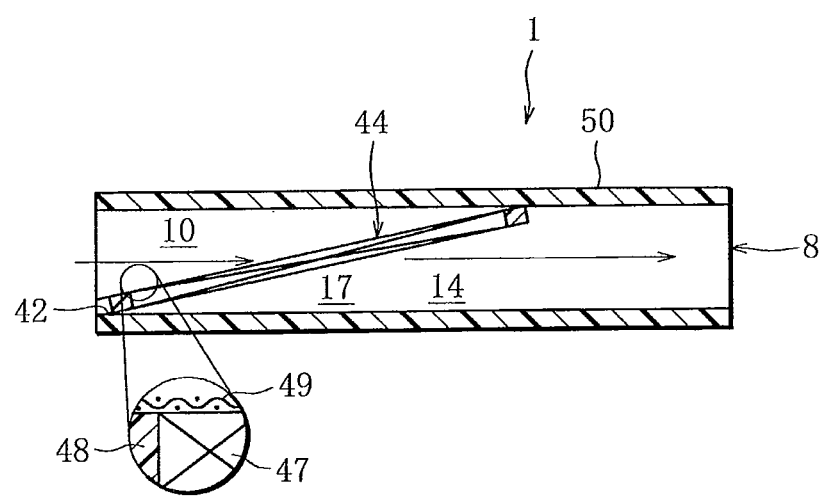
FIG. 18 is a cross-sectional view of an embodiment of a flavor inhaler categorized as group E.
Figure 19:
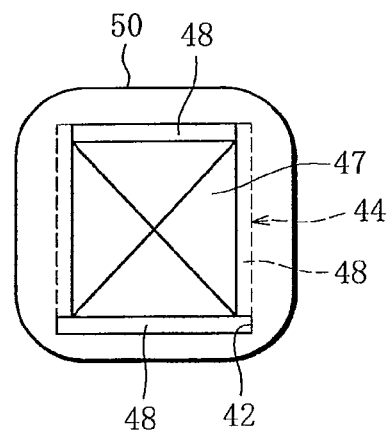
FIG. 19 is a front view of the flavor inhaler shown in FIG. 18.

A flavor inhaler 1 according to embodiment E shown in FIGS. 18 and 19 comprises a hollow suction holder 50 open at either end, and having an air passage 17 approximately square in cross-section. Specifically, as seen in FIG. 18, the air passage 17 is delimited by two side surfaces, a bottom surface and a top surface. The two side surfaces each have a slant groove 42. The grooves 42 each have an open end at the front end of the suction holder 2, near the bottom surface, and extend from their open end to the top surface, parallel to each other.

Inside the suction holder 50, for example a cartridge 44 shown in FIG. 10 is set using the slant grooves 42. Specifically, the cartridge 44 is set in the suction holder 50, in slant position, with the side edges of the holder frame 48 fitted in the slant grooves 42, respectively. The cartridge 44 divides the air passage 17 into an upstream section 10 adjacent to the front end of the suction holder 50 and a downstream section 14 adjacent to the mouth end 8.

Also in the flavor inhaler 1 shown in FIG. 18, the user's sucking on the mouth end 8 causes air to flow into the upstream section 10, via the front end of the suction holder 50, then through the cartridge 44 packed with the particles 47, uniformly in all parts of the particles 47-filled chamber of cartridge 44, and then through the downstream section 14 to the mouth end 8.

Also in this embodiment, the area of the surface of the particles 47-filled chamber of the cartridge 44 exposed on the upstream section 10 side is greater than the cross-sectional area of the suction holder 2, which allows the user to inhale air sufficiently containing flavoring constituents of tobacco released from the particles.

In the above, several embodiments of the present invention have been described. The present invention is however not restricted to the described embodiments but can be altered in various ways without departing from the scope and spirit of the invention.

Figure 20:
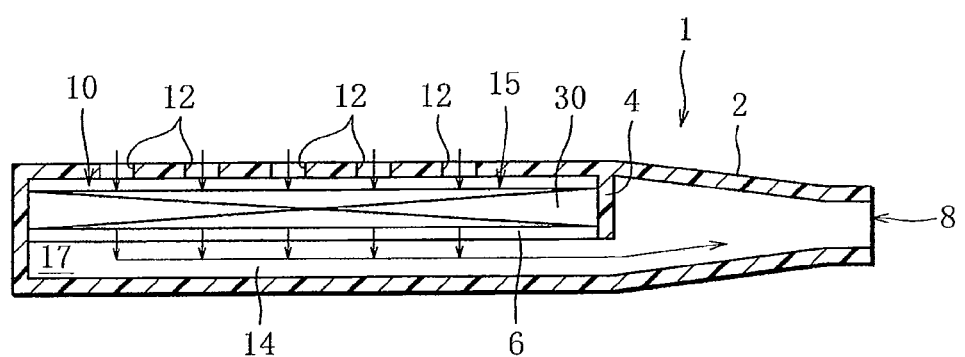
FIG. 20 is a cross-sectional view of another example of a mouthpiece of the suction holder.

For example, the portion providing a mouth end 8, which is circular in shape in the described embodiments, may be tapered as shown in FIG. 20.

The pouch 30 may have particles made from, for example tea leaves so as to be a source for releasing a flavor other than the tobacco flavor.

The suction holder 2 is cylindrical in shape in the described embodiments, but not restricted to the cylindrical shape; it may be of a box shape, for example.

EXPLANATION OF REFERENCE CHARACTERS

1: Flavor inhaler
2: Suction holder
4: Partition
6: Rib
8: Mouth end
10: Upstream section
12, 13: Ambient air intake
14: Downstream section
15: Space
16: Removal opening
17: Air passage
18, 19: Holder frame
20: Opening
21: Lid
22, 23: Groove
24, 26: Half pipe
28: Self-hinge
29a, 29b: Recess, projection
30: Pouch (flavor releasing source)
32: Holder body
33, 34: Half pipe
36: Tubular joint
38: Hole
40: Mouthpiece
42: Slant groove
44: Cartridge
46: Air-permeable case
47: Particle
48: Holder frame
49: Air-permeable sheet
50: Suction holder

The invention claimed is:

1. A non-heating flavor inhaler, comprising:
a hollow suction holder having a longitudinal axis, a front end and a rear end serving as a mouth end, and defining an air passage therein for allowing ambient air taken in at a front end side to flow to the mouth end; and
a flavor releasing source arranged in said suction holder, said flavor releasing source being air-permeable and capable of releasing flavoring substances in the air passage without being ignited,
wherein said flavor releasing source splits the air passage into two regions along the longitudinal axis with respect to a direction of said suction holder,
one of the two regions forms a front end-side upstream section extending from the front end toward the mouth end of said suction holder,
the other of the two regions forms a mouth end-side downstream section, the mouth end-side downstream section including a front passage extending from the front end toward the mouth end of said suction holder along the front end-side upstream section and a rear passage extending from the front passage to the mouth end, the front passage and the front end-side upstream section being located at both sides of the longitudinal axis, and an exposing area of said flavor releasing source is greater than a cross-section of said suction holder delimited by an inner circumference thereof.

2. The inhaler according to claim 1, wherein the upstream section includes an ambient air intake provided in at least one of a circumferential wall and a front end wall of said suction holder to allow ambient air to flow in toward said flavor releasing source.

3. The inhaler according to claim 2, wherein said suction holder includes a pair of half pipes separable from each other along a plane containing the longitudinal axis.

4. The inhaler according to claim 3, wherein said flavor releasing source is integrally joined to one of the half pipes.

5. The inhaler according to claim 3, wherein said suction holder further includes a hinge connecting the half pipes in a manner allowing the half pipes to be opened and closed.

6. The inhaler according to claim 2, wherein
said suction holder further includes a partition determining a position of a mouth end-side end of said flavor releasing source.

7. The inhaler according to claim 1, wherein the upstream section includes a space provided between an inner surface of said suction holder and said flavor releasing source.

8. The inhaler according to claim 1, wherein
said suction holder includes
a holder body providing a part of said suction holder from the front end up to the front passage of the downstream section, and
a mouthpiece providing the rear passage of the downstream section, the mouthpiece being separably connected to the holder body.

9. The inhaler according to claim 8, wherein the holder body has a pair of half pipes separable from each other along a plane containing the longitudinal axis.

10. The inhaler according to claim 9, wherein said flavor releasing source is integrally joined to one of the half pipes.

11. The inhaler according to claim 9, wherein the holder body further has a hinge connecting the half pipes in a manner allowing the half pipes to be opened and closed.

12. The inhaler according to claim 1, wherein said flavor releasing source includes a pouch having particles obtained by shredding or shattering tobacco leaves, and an air-permeable wrapper covering the particles therein.

13. The inhaler according to claim 12, wherein said flavor releasing source further includes a holder frame for holding the pouch.

14. The inhaler according to claim 1, wherein said suction holder has an opening at the front end, and said flavor releasing source being set inside said suction holder through the opening, with an end of said flavor releasing source exposed therein.

15. The inhaler according to claim 14, further comprising a lid operable to cover or uncover the opening.

16. The inhaler according to claim 1, wherein said flavor releasing source includes particles obtained by shredding or shattering tobacco leaves, and a case packed with the particles therein,
the case having two air-permeable surfaces and being arranged in said suction holder with the two air-permeable surfaces extending along the longitudinal axis and facing the upstream and downstream sections, respectively.

* * * * *